(12) United States Patent
Matheus et al.

(10) Patent No.: US 7,960,516 B2
(45) Date of Patent: Jun. 14, 2011

(54) SOLID FORMS OF ANTI-EGFR ANTIBODIES

(75) Inventors: Susanne Matheus, Neumagen-Dhron (DE); Hanns-Christian Mahler, Wiesbaden (DE)

(73) Assignee: Merck Patent GmbH, Darmstadt (DE)

( * ) Notice: Subject to any disclaimer, the term of this patent is extended or adjusted under 35 U.S.C. 154(b) by 304 days.

(21) Appl. No.: 10/580,563

(22) PCT Filed: Nov. 12, 2004

(86) PCT No.: PCT/EP2004/012837
§ 371 (c)(1), (2), (4) Date: May 26, 2006

(87) PCT Pub. No.: WO2005/051355
PCT Pub. Date: Jun. 9, 2005

(65) Prior Publication Data
US 2007/0122411 A1 May 31, 2007

(30) Foreign Application Priority Data
Nov. 29, 2003 (DE) .................. 103 55 904

(51) Int. Cl.
*C12P 21/08* (2006.01)
*C07K 16/00* (2006.01)
(52) U.S. Cl. .................. 530/387.3; 530/388.1
(58) Field of Classification Search .......... None
See application file for complete search history.

(56) References Cited

U.S. PATENT DOCUMENTS

| 5,558,864 A | 9/1996 | Bendig et al. |
|---|---|---|
| 6,217,866 B1 | 4/2001 | Schlessinger et al. |
| 2002/0136719 A1* | 9/2002 | Shenoy et al. ............. 424/130.1 |
| 2002/0197261 A1* | 12/2002 | Li et al. ...................... 424/178.1 |
| 2004/0006212 A1 | 1/2004 | Goldstein et al. |
| 2004/0170632 A1 | 9/2004 | Mahler et al. |

FOREIGN PATENT DOCUMENTS
WO WO 2006/009694 A1 * 1/2006

OTHER PUBLICATIONS

Weber, Overview of Crystallization Methods. Methods in Enzymology, 1997, vol. 276, pp. 13-22.*
Drenth, "Principles of Protein X-Ray Crystallography", 2nd Edition, 1999 Springer-Verlag New York Inc., Chapter 1, p. 1-21.*
McPherson, A. Current Approaches to Macromolecular Crystallization. European Journal of Biochemistry. 1990. vol. 189, pp. 1-23.*
ATCC Index of publically available deposited Hybridoma Cell Lines. Dec. 17, 2008. http://www.atcc.org/Portals/1/Pdf/CellCatalog/Hybridomas.pdf.*
Ahamed et al. Phase Behaviour of Intact Monoclonal Antibody. Biochemical Journal, Jul. 2007, vol. 93, pp. 610-619.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Baselga J: "The EGFR as a Target for Anticancer Therapy-Focus on Cetuximab" European Journal of Cancer, Pergamon Press, Oxford, GB, Bd. 37, Sep. 2001, pp. 16-22, XP004307911; ISSN: 0959-8049.
Abou-Jawde Rony et al: "An Overview of Targeted Treatments in Cancer" Clinical Therapeutics, Bd. 25, Nr. 8, Aug. 2003, pp. 2121-2137, XP002316108; ISSN: 0149-2918.
Hurrell J.G.R.: "Monoclonal Hybridoma Antibodies: Techniques and Applications" 1982, CRC Press, Boca Raton, Florida, XP009043454; p. 51.
Deutscher M.P.: "Guide to Protein Purification" 1990, Academic Press, San Diego, XP002316109, pp. 285-306.

* cited by examiner

*Primary Examiner* — Suzanne M. Noakes
(74) *Attorney, Agent, or Firm* — Millen, White, Zelano, Branigan, P.C.

(57) ABSTRACT

The invention relates to solid forms of antibodies against the EGF receptor, in particular precipitates and crystals of monoclonal antibodies against the EGF receptor, particularly preferably of Mab C225 (cetuximab) and Mab h425 (EMD 72000), which result in biologically active antibody protein through dissolution or suspension in aqueous medium, obtainable by precipitation of the antibody and/or one of its variants and/or fragments dissolved or suspended in aqueous medium by means of a precipitation reagent. The invention furthermore relates to pharmaceutical preparations comprising at least one solid form of above-mentioned antibodies in precipitated non-crystalline, precipitated crystalline or in soluble or suspended form, and optionally excipients and/or adjuvants and/or further pharmaceutical active ingredients, and to a process for the preparation of solid forms of anti-EGFR antibodies according to the invention.

8 Claims, No Drawings

SOLID FORMS OF ANTI-EGFR ANTIBODIES

This application is a 35 U.S.C. §371 National Stage application of International Application No. PCT/EP04/12837 filed on Dec. 11, 2004 and claims priority to DE 103 55 904.3, filed Nov. 29, 2003.

BACKGROUND OF THE INVENTION

The invention relates to solid forms of antibodies against the EGF receptor (EGFR), in particular precipitates and crystals of monoclonal antibodies against the EGF receptor, particularly preferably of Mab C225 (cetuximab) and Mab h425 (EMD 72000), which result in biologically active antibody protein through dissolution or suspension in aqueous or non-aqueous medium, obtainable by precipitation of the antibody and/or one of its variants and/or fragments dissolved or suspended in aqueous medium by means of a precipitation reagent. The invention furthermore relates to pharmaceutical preparations comprising at least one solid form of the above-mentioned antibodies in precipitated non-crystalline, precipitated crystalline or in dissolved or suspended form, and optionally excipients and/or adjuvants and/or further pharmaceutical active ingredients, and to a process for the preparation of solid forms of anti-EGFR antibodies according to the invention.

Advances in the area of biotechnology have made it possible in the course of the last 10 years to prepare a series of proteins for pharmaceutical application by means of recombinant DNA techniques. Protein medicaments, such as monoclonal antibodies, are used, for example, in tumour therapy, for example for specific immunotherapy or tumour vaccination. Therapeutic proteins are larger and more complex than conventional organic and inorganic active ingredients and they have complex three-dimensional structures and numerous functional groups which effect the biological activity of the protein or alternatively can cause undesired effects. During preparation, storage and transport, protein medicaments are exposed to numerous exogenous influences which can have a stability-reducing action on the protein active ingredient. It is therefore necessary to study accurately the causes and mechanisms of the specific degradation reactions in order to be able to stabilise the protein, for example through addition of certain stabilising adjuvants (see, for example, Manning M. C., Patel K., & Borchardt R. T. (1989) Stability of protein pharmaceuticals. Pharm. Res. 6, 903-918).

The literature discloses numerous formulations of therapeutic proteins. However, the requirements of the composition of a pharmaceutical preparation of protein active ingredients may be very different, and in general it is not possible, owing to specific physico-chemical properties and degradation reactions of the different proteins, to apply already established protein formulations to novel protein active ingredients. Suitable pharmaceutical formulations and stable forms of these novel active ingredients are therefore still a major challenge.

Chemical instabilities are distinguished by covalent modifications of the protein. The primary structure of the protein changes through the breaking, new formation or re-formation of chemical bonds. The newly formed substance is generally completely different in biological activity from the original, native protein. Physical instabilities modify the spatial arrangement of the molecule (the secondary, tertiary and quaternary structure) without destroying covalent bonds. They can be divided into denaturing, association, aggregation, precipitation or adsorption. Physical instabilities are a frequent phenomenon, in particular in the case of relatively large proteins. Precipitates are the macroscopically visible equivalent of aggregates and are formed in mechanistic terms by clusters of aggregates or associates. By exceeding the solubility limit and due to precipitation, the flakes become visible from a diameter of about 10 µm through a light microscope and from about 50 µm with the naked eye. Protein aggregation can be a reversible or irreversible process (see, for example, Cleland J. L., Powell M. F. & Shire S. J. (1993) The development of stable protein formulations: A close look at protein aggregation, deamidation, and oxidation. Crit. Rev. Ther. Drug Carrier Syst. 10, 307-377).

Although the previous literature describes the precipitation of proteins with salts, polymers and organic solvents as standard method for the purification of proteins (Scopes R. K. (1997) Separation by Precipitation. In: Protein Purification: Principles and Practice (ed Scopes R. K.), 2 edn, pp. 41-71. Springer Verlag, N.Y.), the use of this method usually results, however, particularly in the case of immunoglobulins, in denaturing, an associated reduction in activity and in poor quantitative yields, in particular on use of salts and organic solvents (Phillips A. P., Martin K. L., & Horton W. H. (1984) The choice of methods for immunoglobulin IgG purification: Yield and purity of antibody activity. Journal of Immunological Methods 74, 385-393). On use of polyethylene glycol (PEG), by contrast, better results are achieved (A. Poison, G. M. Potgieter, J. F. Largier, and G. E. F. Joubert, F. J. Mears. The Fractionation of Protein Mixtures by linear Polymers of High Molecular Weight. Biochim. Biophys. Acta 82:463-475, 1964).

Protein crystals are known from purification processes (downstream processing), preferably of enzymes, and for the elucidation of the tertiary structure of proteins by means of X-ray structural analysis (R. K. Scopes. Analysis for purity: Crystallization. In: Protein Purification: Principles and Practice, edited by R. K. Scopes, New York:Springer Verlag, 1997, p. 284-301). The formation of new ordered intermolecular contacts between proteins occurs here. This is a slow process, with reduced mobility. The concentration of the protein in solution is reduced in the process.

Although the literature describes the crystallisation of proteins with salts, polymers and organic solvents as standard method for elucidation of the structure of immunoglobulins (Harris L. J., Skaletsky E., & McPherson A. (1995) Crystallization of Intact Monoclonal Antibodies. Proteins: Structure, Function, and Genetics 23, 285-289; Harris L. J., Skaletsky E., & McPherson A. (1998) Crystallographic Structure of an Intact Ig1 Monoclonal Antibody. Journal of Molecular Biology 275, 861-872; Edmundson A. B., Guddat L. W., & Andersen K. N. (1993) Crystal Structures of intact IgG antibodies. ImmunoMethods 3, 197-210), the crystallisation of intact, for example glycosylated antibodies is, however, extremely difficult since the size of the protein, the different glycosylation pattern of the individual anti-body molecules and the associated microheterogeneities as well as the structural flexibility of the immunoglobulin make ordered incorporation into a crystal lattice more difficult or even prevent it (McPherson A. (1999) Crystallization of Biological Macromolecules, 1 edn. Cold Spring Harbor Laboratory Press, New York). In addition, antibody molecules exhibit a tendency towards aggregation, which likewise causes great difficulties in crystallisation (McPherson A. (1999) Crystallization of Biological Macro-molecules, 1 edn. Cold Spring Harbor Laboratory Press, New York). In addition, the risk of denaturing of the antibodies during the crystallisation process makes the crystallisation of therapeutic antibodies unattractive to the person skilled in the art. Thus, only a few intact antibodies have hitherto been crystallised for structural elucidation and only three antibodies have hitherto been crystallised on a preparative scale. Thus, the immunoglobulins listed in the Biological Macromolecule Crystallization Database (Gilliland, G. L., Tung, M., Blakeslee, D. M. and Ladner, J. 1994. The Biological Macromolecule Crystallization Database, Version 3.0: New Features, Data, and the NASA Archive for Protein Crystal Growth Data. Acta Crystallogr. D50 408-413.) which have already been crystallised are principally Fab and Fc fragments.

WO02072636 describes antibody crystals, which, however, are prepared in a complex process with inoculation and using detergents, which should be avoided as far as possible in pharmaceutical formulations, and adjuvants, some of which are toxicologically unacceptable. In addition, the partide size cannot be controlled in the process described. In a control experiment (see Example 8), it was possible to show that the needle-shaped crystals described are obtained both from the protein solution and from the negative control (without protein) using the process described in WO02072636. It is clear from this that these are presumably at best protein inclusions in crystals of the precipitation reagent.

For the above-mentioned reasons, it is clear that crystallisation of anti-bodies is extremely difficult for the person skilled in the art and crystallisation processes disclosed in the literature cannot be applied to all known antibodies owing to the considerable heterogeneity of the different known antibodies with respect to primary, secondary and tertiary structure, glycosylation and structural flexibility. It was likewise unattractive to the person skilled in the art, for the above-mentioned reasons, to prepare precipitates of therapeutic antibodies since, in particular, irreversible denaturing was to be expected.

The object of the present invention was therefore to find stable forms, for example precipitates or crystals, for therapeutic proteins, in particular anti-bodies, so that their efficacy is retained during preparation, storage, transport and application. Since, as mentioned above, already established protein formulations generally cannot be applied to novel protein active ingredients, it was a further object of the present invention to find novel stable formulations for monoclonal antibodies against the EGF receptor, for example Mab C225 (cetuximab) and Mab h425 (EMD 72000). Although formulations comprising Mab C225 (cetuximab) or Mab h425 (EMD 72000) are disclosed in WO03053465 and WO 03/007988, the formulations disclosed in WO03053465 have, however, a relatively low protein concentration and they are not long-term-stable at room temperature, and the formulations disclosed in WO03007988 likewise have a relatively low protein concentration and the preparation (lyophilisate) has to be reconstituted before use. Consequently, a further object of the present invention was to find a stable pharmaceutical preparation which has a high concentration of the above-mentioned antibodies.

The process of lyophilisation for the stabilisation of protein formulations is disclosed, for example, in WO9300807 and WO9822136, but significant disadvantages of lyophilised preparations consist in that the user has to reconstitute the lyophilisate before use, which represents a considerable source of error in the preparation before use. Since a further preparation process is added compared with liquid formulations, the process is unfavourable with respect to additional work for process development (ensuring the stability during lyophilisation), preparation (preparation costs and duration) and, for example, validation.

The object of the present invention was thus to find solid forms and formulations for above-mentioned antibodies which have increased stability to stress conditions, such as elevated temperature, atmospheric humidity and/or shear forces, and comprise no toxicologically unacceptable adjuvants.

SUMMARY OF THE INVENTION

Surprisingly, it has been found that solid forms of the above-mentioned antibodies can be prepared and these solid forms and formulations prepared therefrom do not have the disadvantages mentioned in the prior art. The solid forms of anti-EGFR antibodies according to the invention described below and/or the formulations prepared therefrom are distinguished, surprisingly, by one or more advantages selected from: high stability, controllable particle size, native and biologically active protein after re-dissolution or resuspension, high purity, absence of pharmaceutically unacceptable agents and thus high safety, good tolerability and possibility of direct use, low aggregation tendency and thus the possibility of the preparation of highly concentrationed formulations, and low viscosity on formulation as a protein suspension compared with a solution. The preparation process according to the invention described below is distinguished, surprisingly, by one or more advantages selected from: simplicity, saving of time and costs, use of pharmaceutically acceptable agents, high yield. The process according to the invention can thus preferably be carried out in a significantly simpler, time-saving and cost-effective manner than the techniques described in the literature since only the addition of a single precipitation reagent is necessary.

In addition, the precipitation reagent is added to a solution of the antibody in a suitable buffer system, i.e. stabilisation of the reaction solutions by further adjuvants, such as, for example, detergents, is not necessary. The use of detergents in preparations for parenteral administration should generally be avoided or minimised since they cause a not inconsiderable toxic and immunogenic potential (Sweetana S. & Akers M. J. (1996) Solubility principles and practices for parenteral drug dosage form development. PDA J. Pharm. Sci. Technol. 50, 330-342) and they can also result in a change in the secondary structure of proteins (Vermeer A. W. P. & Norde W. (2000) The influence of the binding of low molecular weight surfactants on the thermal stability and secondary structure of IgG. Colloids and Surfaces A: Physicochemical and Engineering Aspects 161,139-150). Thus, the resultant solid forms of anti-EGFR antibodies can be used directly in medicaments, and further purification for the removal of pharmacologically unacceptable agents is not necessary. By contrast, the crystals obtained in WO02072636 have to be freed from pharmacologically unacceptable agents, for example CHES, imidazole, TRIS, manganese(II) chloride, zinc(II) chloride, copper(II) sulfate, 2-propanol, 2-methoyl-2,4-pentanediol, HEPES, lithium sulfate, ethoxyethanol or detergents, such as polysorbate 80 or 20, in a complex process or it is even impossible completely to remove the above-mentioned unacceptable agents.

Surprisingly, it has been found that preferably stable solid forms are obtained if antibodies against the EGF receptor (anti-EGFR antibodies), preferably monoclonal anti-EGFR antibodies, particularly preferably Mab C225 (cetuximab) or Mab h425 (EMD 72000), are incubated at suitable pH and suitable temperature in the presence of a suitable buffer with the aid of certain precipitation reagents selected from polymers, preferably polyethylene glycol (PEG), salts, preferably ammonium sulfate, or organic solvents, preferably ethanol, or mixtures thereof.

Surprisingly, it has been found that the solid forms of anti-EGFR antibodies, preferably of monoclonal anti-EGFR antibodies, particularly preferably of Mab C225 (cetuximab) or Mab h425 (EMD 72000), and/or variants or fragments thereof, obtained by the process according to the invention are preferably native after redissolution and are preferably obtained in a high yield.

The invention therefore relates to solid forms of anti-EGFR antibodies and/or variants or fragments thereof which result in biologically active antibody protein through dissolution or suspension in aqueous medium, obtainable by precipitation of the antibody and/or one of its variants and/or fragments dissolved or suspended in aqueous medium by means of a precipitation reagent selected from polymers, preferably polyethylene glycol (PEG), salts, preferably ammonium sulfate, or organic solvents, preferably ethanol, or mixtures thereof, in the presence of a suitable buffer, at suitable pH and suitable temperature.

Solid Forms of Anti-EGFR Antibodies:

The expression "solid forms of an anti-EGFR antibody according to the invention" is preferably taken to mean precipitates or crystals which result in a biologically active antibody through dissolution or suspension in aqueous or non-aqueous medium.

Solid forms according to the invention are obtained by precipitation of the antibody dissolved or suspended in an aqueous medium in accordance with the process described below. The solid forms according to the invention can be in the μm and nm ranges.

Precipitates:

For the purposes of the present invention, the term precipitates is taken to mean solid forms in an amorphous non-crystalline structure or aggregation and association states.

Crystals:

For the purposes of the present invention, the term crystals is taken to mean solid forms in a crystalline structure.

Crystalline structures can be detected using the following processes.

precipitated: for the purposes of the present invention, the term precipitated is taken to mean solid forms according to the invention in precipitated form, i.e. in the form of a precipitate or crystal, depending on the process conditions.

precipitated crystalline: for the purposes of the present invention, the term precipitated crystalline or crystalline is taken to mean solid forms according to the invention in an ordered crystalline structure.

precipitated non-crystalline: for the purposes of the present invention, the term precipitated non-crystalline is taken to mean solid forms according to the invention in amorphous non-crystalline structures or aggregation and association states.

dissolved: for the purposes of the present invention, the term dissolved form is taken to mean solid forms according to the invention which are dissolved or redissolved in a solution according to the invention.

suspended: the term suspended form is taken to mean solid forms according to the invention which are suspended or resuspended in a solution according to the invention.

For the purposes of the invention, "aqueous medium" is taken to mean water or mixtures of water with suitable inert solvents and other agents mentioned in Example 1, such as, for example, buffers, stabilisers or adjuvants, having the property that aqueous media according to the invention do not on their own result in the precipitation or crystallisation of the anti-body, but instead precipitation or crystallisation only takes place through addition of precipitation reagents according to the invention.

For the purposes of the invention, "non-aqueous medium" is taken to mean oils or mixtures of oils with water or other suitable inert solvents and other agents mentioned in Example 1, such as, for example, stabilisers or adjuvants, having the property that non-aqueous media according to the invention do not alone result in the precipitation or crystallisation of the antibody, but instead precipitation or crystallisation only takes place through addition of precipitation reagents according to the invention.

With respect to the anti-EGFR antibodies according to the invention and for the purposes of the present invention, the terms "biologically active", "native" and "effective" are taken to mean that anti-EGFR antibodies according to the invention are able to exert their biological effect even after conversion into solid forms according to the invention and subsequent redissolution or resuspension, in particular the binding to EGFR, inhibition of the binding of ligands, in particular EGF, to the EGFR, modulation, in particular inhibition of EGFR-mediated signal transduction and prophylaxis or therapy of EGFR-mediated diseases.

In particular, straightforward preparation of crystals of anti-EGFR antibodies according to the invention was therefore not to be expected since antibodies generally have a strong tendency towards aggregation, which makes ordered incorporation into a crystal lattice more difficult or even prevents it (McPherson A. (1999) Crystallization of Biological Macromolecules, 1 edn. Cold Spring Harbor Laboratory Press, New York). In spite of the difficulties to be expected for the person skilled in the art in the crystallisation of antibodies according to the invention owing to the above-mentioned inhomogeneity with respect to the protein structure, glycosylation and structural segmental flexibility, even within an antibody species, excellent results are, surprisingly, achieved by means of the process according to the invention.

The high stability of the resultant crystals of antibodies according to the invention is also characterised in that neither a change in the particle shape and particle size spectrum, which would be regarded as crucial with respect to immunogenic side effects, nor changes in the primary structure or secondary structure of the protein occur. The process according to the invention thus offers the advantage that the particle size of the resultant crystals is preferably controllable and stable three-dimensional crystals are preferably obtained. The crystal size can be in the μm and nm ranges.

anti-EGFR antibodies: anti-EGFR antibodies according to the invention are preferably monoclonal and of murine or human origin; they are particularly preferably of murine origin and are chimeric or humanised. The antibody directed against the receptor of epidermal growth factor (EGFR) is particularly preferably Mab C225 (cetuximab) or Mab h425 (EMD 72000) and/or variants or fragments thereof. Further antibodies directed against EGFR are described, for example, in EP 0586002 and in J. Natl. Cancer Inst. 1993, 85: 27-33 (Mab 528).

Mab C225 (cetuximab, Erbitux™): Mab C225 (cetuximab) is a clinically proven antibody which binds to the EGF receptor. Mab C225 (cetuximab) is a chimeric antibody whose variable regions are of murine origin and whose constant regions are of human origin. It was described for the first time by Naramura et al., Cancer Immunol. Immunotherapy 1993, 37: 343-349 and in WO 96/40210 A1.

Mab h425 (EMD 72000): Mab h425 (EMD 72000) is a humanised monoclonal antibody (Mab) obtained from the murine anti-EGFR antibody 425 (Mab 425) (EP 0531472). The murine monoclonal antibody Mab 425 was developed in the human carcinoma cell line A431, since it binds here to an extracellular epitope of the epidermal growth factor receptor (EGFR). It has been found that it inhibits the binding of EGF (Murthy et al., 1987). Increased expression of EGFR is found in malignant tissues from various sources, and consequently Mab 425 is a possible active ingredient for the diagnosis and therapeutic treatment of human tumours. Thus, it has been found that Mab 425 mediates tumour cytotoxicity in vitro and suppresses tumour growth of cell lines of epidermoid and colorectal carcinomas in vitro (Rodeck et al., 1987). In addition, it has been shown that Mab 425 binds to xenografts of human malignant gliomas in mice (Takahashi et al., 1987). Its humanised and chimeric forms are disclosed, for example, in EP 0531472; Kettleborough et al., Protein Engineering 1991, 4: 773-783; Bier et al., Cancer Chemother Pharmacol. 2001, 47: 519-524; Bier et al., Cancer Immunol. Immunother. 1998, 46: 167-173. Mab h425 (EMD 72000) is a humanised antibody (h425) which is in clinical phase I/II and whose constant region is composed of a K and a human γ-1 chain (EP 0531472).

Human anti-EGFR antibodies can be prepared by the XenoMouse technology, as described in WO9110741, WO9402602 and WO9633735. An antibody undergoing clinical trials which was prepared by this technology is, for example, ABX-EGF (Abgenix, Crit. Rev. Oncol. Hematol. 2001, 38: 17-23; Cancer Research 1999, 59: 1236-43).

Antibody: antibody or immunoglobulin is used in the broadest sense for the purposes of the present invention and relates, in particular, to polyclonal antibodies and multispecific antibodies (for example bispecific antibodies) and particularly preferably intact monoclonal antibodies (Mab) which are biologically active, and variants and fragments thereof. The term also covers heteroantibodies which consist of two or more antibodies or fragments thereof and/or have different binding specificities and are bound to one another. Depending on the amino acid sequence of their constant regions, antibodies can be assigned to different "antibody (immunoglobulin) classes: IgA, IgD, IgE, IgG and IgM. A number of these can be further subdivided into sub-classes (isotypes), for example IgG1, IgG2, IgG3, IgG4, IgA1 and IgA2. Antibodies usually have a molecular weight of about 150 kDa, consist of two identical light chains (L) and two identical heavy chains (H). Monoclonal antibodies are obtained from a population of homogeneous cells. They are highly specific and directed against a single epitope, while polyclonal antibodies cover different antibodies which are directed against different epitopes. Processes for the preparation of monoclonal antibodies include, for example, the hybridoma method described by Kohler and Milstein (Nature 256, 495 (1975)) and in Burdon et al., (1985) "Monoclonal Antibody Technology, The Production and Characterisation of Rodent and Human Hybridomas", Eds, Laboratory Techniques in Biochemistry and Molecular Biology, Volume 13, Elsevier Science Publishers, Amsterdam. They can be prepared, in particular, by known recombinant DNA techniques (see, for example, U.S. Pat. No. 4,816,567). Monoclonal antibodies can also be isolated from phage antibody libraries, for example with the aid of the techniques described in Clackson et al. (Nature, 352:624-628 (1991)) and Marks et al. (J. Mol. Biol., 222:58, 1-597(1991)).

Variants and fragments: variants (muteins) of antibodies are structurally related proteins, for example those which can be obtained by modification of the primary sequence (amino acid sequence), by glycoengineering (variants of the glycosylation sites or structures, also deglycosylated proteins), by PEGylation, by preparation in modified host cells or by other techniques. Variants according to the invention are not restricted here to the above examples, but instead include all variants of antibodies according to the invention which are known to the person skilled in the art. Fragments (partial segments) of antibodies are cleavage products of antibodies obtained, for example, by limited enzymatic digestion with the aid of papain, pepsin and plasmin or by preparation of the partial segments by genetic engineering. Typical partial segments are, for example, the bivalent $F(ab')_2$ fragment, the monovalent Fab fragment and the Fc fragment. (Lottspeich F., H. Zorbas (ed.). Bioanalytik, Heidelberg; Berlin: Spektrum AkademischerVerlag GmbH, (1998) pp. 1035). Fragments according to the invention are not restricted here to the above examples, but instead include all fragments of antibodies according to the invention which are known to the person skilled in the art.

Pharmaceutical preparation: the terms pharmaceutical formulation and pharmaceutical preparation are used synonymously for the purposes of the present invention.

As used here, "pharmaceutically tolerated" relates to medicaments, precipitation reagents, excipients, adjuvants, stabilisers, solvents and other agents which facilitate the administration of the pharmaceutical preparations obtained therefrom to a mammal without undesired physiological side effects, such as nausea, dizziness, digestion problems or the like.

In pharmaceutical preparations for parenteral administration, there is a requirement for isotonicity, euhydria and tolerability and safety of the formulation (low toxicity), of the adjuvants employed and of the primary packing. Surprisingly, solid forms of anti-EGFR antibodies according to the invention preferably have the advantage that direct use is possible, since the precipitation reagents used are physiologically acceptable agents and thus further purification steps for the removal of toxicologically unacceptable agents, such as, for example, high concentrations of organic solvents or other toxicologically unacceptable adjuvants, are unnecessary before use of the solid forms according to the invention in pharmaceutical formulations. The preparation of solid forms of anti-EGFR antibodies according to the invention with preferably simultaneously a high yield of native and pharmaceutically acceptable protein of high purity is thus preferably simple, time-saving and inexpensive.

The invention therefore also relates to a process for the preparation of a solid form of an anti-EGFR antibody according to the invention and/or one of its variants and/or fragments which results in biologically active antibody protein through dissolution or suspension in aqueous medium, characterised in that the antibody and/or variants and/or fragments thereof dissolved or suspended in aqueous solution are precipitated by means of a precipitation reagent, and the precipitation product is separated off. The precipitation reagents used in the process according to the invention are preferably polymers, particularly preferably polyethylene glycol (PEG), salts, particularly preferably ammonium sulfate, or organic solvents, particularly preferably ethanol.

A solid form of an anti-EGFR antibody according to the invention can be prepared by adding the precipitation reagents according to the invention mentioned in Example 1, preferably polymers, such as particularly preferably polyethylene glycol (PEG) in a concentration of from 0.1 to 99.9% (w/v), having an average molecular weight of 200-80,000, preferably 400 to 20,000, particularly preferably 400-8000; salts, such as particularly preferably ammonium sulfate in a concentration of 0.1-4.5 M, sodium acetate trihydrate in a concentration of 0.1-4.5 M, trisodium citrate dihydrate in a concentration of 0.1-1.5 M, potassium phosphate in a concentration of 0.1-1.2 M, potassium chloride in a concentration of from 0.1 to 4.7 M, sodium chloride in a concentration of from 0.1 to 6.1 M, dipotassium hydrogenphosphate in a concentration of from 0.1 to 3.0 M, disodium hydrogenphosphate dihydrate in a concentration of from 0.1 to 0.5 M, or organic solvents, such as particularly preferably ethanol in a concentration of 0.1-99.9% (v/v), or mixtures thereof, and adjuvants, buffers and/or stabilisers, to a solution comprising antibodies according to the invention in a batch method, and incubating the mixture at pH values and temperatures mentioned in Example 1. To this end, defined volumes of stock solutions comprising the precipitation reagents, adjuvants, buffers and/or stabilisers mentioned in Example 1 in defined concentration are advantageously added to a solution having a defined concentration of EGFR antibodies (from 0.01 to 150 mg/ml, preferably from 2 to 100 mg/ml, particularly preferably about 5-20 mg/ml), as obtained in its preparation, and optionally diluted with water or buffer (for example citrate or phosphate buffer, in a concentration of from 1 mM to 200 mM, preferably from 2 to 20 mM, particularly preferably about 10 mM; also with addition of isotonicity agents, such as, for example, potassium chloride, sodium chloride in a concentration of 1-1000 mM, preferably 40 mM-310 mM) to the pre-calculated concentration. Alternatively, precipitation reagents, adjuvants, buffers and stabilisers according to the invention can also be added in solid form. If the antibody is itself in the solid aggregate state, for example as a lyophilisate, the solid forms of anti-EGFR antibodies according to the invention can be prepared by firstly dissolving antibodies according to the invention in water or in an aqueous solution comprising one or more further ingredients, and subsequently adding defined volumes of stock solutions comprising the precipitation reagents, adjuvants, buffers and/or stabilisers mentioned in Example 1 in defined concentration. Precipitation reagents, adjuvants, buffers and/or stabilisers according to the invention may in addition also be added in the solid aggregate state. Antibodies according to the invention can advantageously also be dissolved directly in a solution comprising all precipitation reagents, adjuvants, buffers and/or stabilisers.

The invention also covers all hydrates, salts and derivatives of the above-mentioned agents which are known and conceivable to the person skilled in the art.

One or more of the agents mentioned in the invention can advantageously be added during or after completion of the precipitation process and optionally removed again in order, for example, to carry out an additional purification step.

One or more of the precipitation reagents, adjuvants, buffers and/or stabilisers mentioned in the invention can advantageously be added during or after completion of the preparation process of the antibody. This can preferably be carried out by dissolving the antibody according to the invention directly in an aqueous solution comprising one, a plurality or all of the further precipitation reagents, adjuvants, buffers and/or stabilisers in the final step of the purification taking place after the preparation thereof. For the preparation of a pharmaceutical preparation according to the invention, the respective further ingredient(s) then only has (have) to be added in the respective smaller amount or not at all. It is particularly preferred if the respective ingredient is dissolved in an aqueous solution comprising all further precipitation reagents, adjuvants, buffers and/or stabilisers in the final step of the purification of the antibody following preparation thereof. Thus, a solution to be packaged or lyophilised directly can advantageously be obtained. The resultant solution comprising the respective antibody is adjusted to a pH of from 4 to 10, preferably from pH 5 to 9, sterile-filtered and, if necessary, freeze-dried.

The reaction is carried out by methods known to the person skilled in the art in a suitable solvent, in particular in an inert solvent. Suitable inert solvents are ethanol, glycerol, mixtures with water or pure water or water comprising other adjuvants, such as, for example, salts having a buffering or isotonicity-producing action. Particular preference is given to water.

The process described here can particularly preferably be carried out in batch format. Solid forms of anti-EGFR antibodies according to the invention and/or variants and/or fragments thereof prepared by the process according to the invention can particularly preferably be converted into biologically active antibody protein through dissolution or suspension in aqueous medium. To this end, an antibody and/or one of its variants and/or fragments dissolved or suspended in aqueous solution is particularly preferably precipitated by means of a precipitation reagent mentioned in Example 1, and the precipitation product is separated off.

Depending on the choice of concentration of the precipitation reagent, either amorphous precipitates or crystals are obtained. Precipitates are preferably obtained at relatively high concentration of the precipitation reagent, while crystals are preferably obtained at relatively low concentration of the precipitation reagent. Through a suitable choice of the concentration of the precipitation reagent, the concentration of the protein, the other agents according to the invention, the pH and the temperature, the reaction can thus be directed in the desired direction. Examples 2 and 3 give illustrative crystallisation conditions for Mab C225 (Erbitux™), and Examples 4 and 5 give illustrative precipitation conditions. The precipitation process according to the invention and the crystallisation process according to the invention can also be combined.

Suitable reaction temperatures are temperatures of from −10 to 40° C., preferably from 0 to 25° C. and very particularly preferably from 4 to 20° C. The pressure used is preferably from 1 to 20 bar, particularly preferably atmospheric pressure. The pH used is preferably from 4 to 10. The duration of the reaction depends on the reaction conditions selected. In general, the reaction duration is from 0.5 hour to 10 days, preferably from 1 to 24 hours, particularly preferably from 2 to 12 hours.

The term solvates of the solid forms according to the invention is taken to mean adductions of inert solvent molecules onto the solid forms according to the invention which form owing to their mutual attractive force. Solvates are, for example, hydrates, such as monohydrates or dihydrates, or alcoholates, i.e. addition compounds with alcohols, such as, for example, with ethanol.

The resultant solid forms of anti-EGFR antibodies according to the invention can be separated from the corresponding solution in which they are prepared (for example by centrifugation and washing) and, after separation, can be stored in a different composition or they can remain directly in the preparation solution. The resultant solid forms according to the invention can also be taken up in desired solvents for the particular use. The solid forms of anti-EGFR antibodies according to the invention are preferably biologically active after redissolution or resuspension, and denaturing of the antibodies preferably does not occur in the process according to the invention. The biological efficacy of the protein is thus preferably retained.

It has surprisingly likewise been found that stable pharmaceutical formulations can be prepared with the aid of solid forms of anti-EGFR antibodies according to the invention. These formulations preferably have higher stability to physicochemical influences, such as, for example, oxidation, mechanical stresses, unfavourable pH values and temperatures, than conventional protein solutions of antibodies. A comparable stability can otherwise usually only be achieved by expensive and time-consuming methods, such as, for example, the addition of stabilisers, cool storage, freezing or freeze-drying. The high stability preferably facilitates simpler and less expensive storage, transport and preparation of pharmaceutically valuable formulations, such as, for example, ready-to-use formulations, formulations having delayed release of active ingredient or controlled release over an extended period.

The invention therefore furthermore relates to solid forms of anti-EGFR antibodies according to the invention as storage-stable medicaments.

The invention particularly preferably also relates to pharmaceutical preparations comprising at least one solid form of an anti-EGFR antibody according to the invention in precipitated non-crystalline, precipitated crystalline or in dissolved or suspended form, and optionally excipients and/or adjuvants and/or further pharmaceutical active ingredients.

Pharmaceutical preparations according to the invention can thus comprise solid forms according to the invention in precipitated form, i.e. as precipitate or as crystal, or in redissolved or resuspended form. The invention therefore also relates to pharmaceutical preparations comprising at least one precipitate and/or crystal of an anti-EGFR antibody, preferably of a monoclonal anti-EGFR antibody, particularly preferably of Mab C225 (cetuximab) or Mab h425 (EMD 72000) and/or variants or fragments thereof in precipitated, redissolved or suspended form as well as optionally excipients and/or adjuvants and/or further pharmaceutical active ingredients.

The solid forms of anti-EGFR antibodies according to the invention preferably enable the preparation of highly concentrated formulations without unfavourable undesired aggregation of the antibodies according to the invention or undesired high viscosity occurring, as may be observed in the case of conventional, highly concentrated protein solutions. Thus, ready-to-use solutions having a high active-ingredient content can be redissolved or resuspended in aqueous solvents or in aqueous media with the aid of solid forms of anti-EGFR antibodies according to the invention. Extremely highly concentrated formulations of protein active ingredients are recently being demanded to an increased extent. Most antibodies employed for therapy are used in doses in the mg/kg region. A high dose and small volumes to be administered (for example from about 1 to 1.5 ml for subcutaneous administration) show the demand for highly concentrated protein preparations having concentrations of greater than 100 mg/ml. In addition, highly concentrated protein formulations can have considerable advantages in preclinical trials for the investigation of acceptability and efficacy in vitro and in vivo (in an animal model), in clinical trials for investigation of acceptability and efficacy in humans and in clinical use of the product (in particular on subcutaneous administration). Their advantages consist, in particular, in that a relatively small volume of the preparation has to be used. In contrast to infusion or injection of protein medicaments with a relatively low concentration, this enables, for example, subcutaneous administration of protein medicaments for the patient. Subcutaneous administration of protein medicaments can have various reasons. For example, specific targeting in connection with a "therapeutic window" may be desired. Furthermore, subcutaneous administration has the advantage that the patient can carry out the administration himself without being reliant on medical personnel. The example of insulin clearly shows these advantages. However, since the injections for subcutaneous administration can be a maximum of 1-1.5 ml, highly concentrated protein formulations containing more than 100 mg/ml are frequently necessary.

Surprisingly, highly concentrated pharmaceutical preparations which enable protein concentrations of preferably 10-200 mg/ml, particularly preferably of 50-150 mg/ml, in a liquid formulation can be obtained with the aid of solid forms of anti-EGFR antibodies according to the invention. This was unexpected since the tendency towards instability is far greater in highly concentrated protein formulations than in dilute protein formulations (Fields, G., Alonso, D., Stiger, D., Dill, K. (1992) "Theory for the aggregation of proteins and copolymers." J. Phys. Chem. 96, 3974-3981). The "packing density" of the protein molecules is increased at a high protein concentration. An increased number of collisions must accordingly be assumed, and occasional protein associations may occur. This process generally takes place through nucleation and growth mechanisms in which the critical nuclei are often soluble associated proteins which, however, can rapidly be converted into insoluble protein precipitates (denatured protein) (Reithel, J. F. (1962) "The dissociation and association of protein structures", Adv. Protein Chem. 18, 123). The size of the protein aggregates increases with increasing protein concentration, as has already been shown for β-lactoglobulin (Roefs, S. P. F. M., De Kruif, K. G. (1994) "A model for the denaturation and aggregation of β+-lactoglobulin." Eur. J. Biochem. 226, 883-889).

The limit in known highly concentrated formulations of immunoglobulins is normally 2-50 mg/ml (Humira®) in ready-to-use liquid formulations of antibodies With the solid forms according to the invention, however, stable, highly concentrated formulations can be prepared, which was unexpected. Thus, the step of precipitation or crystallisation can give a highly concentrated stable antibody formulation which, after resuspension or redissolution, has reduced viscosity compared with liquid antibody formulations of the same concentration and thus simplifies handling in the case of parenteral administration.

The invention therefore also relates to pharmaceutical preparations comprising at least one solid form of an anti-EGFR antibody according to the invention and/or one of its variants and/or fragments in precipitated non-crystalline, precipitated crystalline or in dissolved or suspended form, where the antibody present is biologically active, characterised in that the antibody concentration is preferably 10-200 mg/ml, particularly preferably 50-150 mg/ml.

The invention also relates to a process for the preparation of a highly concentrated pharmaceutical preparation according to the invention, characterised in that at least one solid form of an anti-EGFR antibody according to the invention and/or one of its variants and/or fragments is dissolved or resuspended in a solution according to the invention, and the antibody concentration is preferably 10-200 mg/ml, particularly preferably 50-150 mg/ml.

Aqueous preparations can be prepared by dissolving or suspending solid forms of anti-EGFR antibodies according to the invention in an aqueous solution and optionally adding adjuvants. To this end, defined volumes of stock solutions comprising the said further adjuvants in defined concentration are advantageously added to a solution or suspension having a defined concentration of solid forms according to the invention, and the mixture is optionally diluted with water to the pre-calculated concentration. Alternatively, the adjuvants can be added in solid form. The amounts of stock solutions and/or water which are necessary in each case can subsequently be added to the aqueous solution or suspension obtained.

Solid forms of anti-EGFR antibodies according to the invention can also advantageously be dissolved or suspended directly in a solution comprising all further adjuvants.

Antibody-containing solutions or suspensions having a pH of from 4 to 10, preferably having a pH of from 5 to 9, and an osmolality of from 250 to 350 mOsmol/kg can advantageously be prepared from the solid forms according to the invention by reconstitution with aqueous solvents. The resuspended or redissolved preparation can thus be administered directly substantially without pain intravenously, intraarterially and also subcutaneously. In addition, the preparation may also be added to infusion solutions, such as, for example, glucose solution, isotonic saline solution or Ringer solution, which may also contain further active ingredients, thus also enabling relatively large amounts of active ingredient to be administered.

Pharmaceutical preparations according to the invention may also comprise mixtures of precipitates and/or crystals according to the invention in precipitated or crystalline and/or redissolved or resuspended form.

The preparations according to the invention are physiologically well tolerated, easy to prepare, can be dispensed precisely and are preferably stable with respect to assay, decomposition products and aggregates throughout storage and transport and during multiple freezing and thawing processes. They can preferably be stored in a stable manner over a period of at least three months to two years at refrigerator temperature (2-8° C.) and at room temperature (23-27° C.) and 60% relative atmospheric humidity (R.H.). Surprisingly, the preparations according to the invention re preferably stable on storage for at least six months even at elevated temperatures and atmospheric humidities, for example at a temperature of 40° C. and 75% relative atmospheric humidity.

For example, solid forms according to the invention can be stored in a stable manner by drying and when necessary converted into a ready-to-use pharmaceutical preparation by dissolution or suspension. Possible methods for drying are, for example, without being restricted to these examples, nitrogen-gas drying, vacuum-oven drying, lyophilisation, washing with organic solvents and subsequent air drying, liquid-bed drying, fluidised-bed drying, spray drying, roller drying, layer drying, air drying at room temperature and further methods.

The term "effective amount" denotes the amount of a medicament or of a pharmaceutical active ingredient which causes a biological or medical response in a tissue, system, animal or human which is sought or desired, for example, by a researcher or physician.

In addition, the term "therapeutically effective amount" denotes an amount which, compared with a corresponding subject who has not taken this amount, has the following consequence: improved treatment, healing, prevention or elimination of a disease, syndrome, disease state, complaint, disorder or prevention of side effects or also the reduction in the progress of a disease, complaint or disorder. The term "therapeutically effective amount" also encompasses the amounts which are effective for increasing normal physiological function.

Medicaments can be administered in the form of dosage units which comprise a predetermined amount of active ingredient per dosage unit. A unit of this type can comprise, for example, from 0.5 mg to 1 g, preferably from 1 mg to 800 mg, of an active ingredient according to the invention, depending on the disease state treated, the method of administration and the age, weight and health of the patient. Preferred dosage unit formulations are those which comprise a daily dose or sub-dose, as indicated above, or a corresponding fraction thereof of an active ingredient. Furthermore, medicaments of this type can be prepared by means of one of the processes generally known in the pharmaceutical sector.

Medicaments can be adapted for administration by any desired suitable route, for example by the oral (including buccal or sublingual), rectal, pulmonary, nasal, topical (including buccal, sublingual or transdermal), vaginal or parenteral (including subcutaneous, intramuscular, intravenous or intradermal) routes. Medicaments of this type can be prepared by means of all processes known in the pharmaceutical sector by, for example, combining the active ingredient with the excipient(s) or adjuvant(s).

Parenteral administration is preferably suitable for administration of the medicaments according to the invention. In the case of parenteral administration, intravenous and subcutaneous administration are particularly preferred. In the case of intravenous administration, the injection can take place directly or also as an addition to infusion solutions.

Medicaments for subcutaneous administration are particularly suitable since stable, highly concentrated formulations can be prepared with the aid of solid forms of anti-EGFR antibodies according to the invention. The highly concentrated formulations necessary for parenteral or subcutaneous administration and small volumes to be administered can thus be achieved.

Subcutaneous administration has the advantage that the patient can administer the medicament himself without expert medical aid. Solid forms of anti-EGFR antibodies according to the invention are also suitable for the preparation of medicaments to be administered parenterally having slow, sustained and/or controlled release of active ingredient. The precipitates and/or crystals according to the invention are preferably in the form of a suspension here and dissolve over an extended and/or controlled period and are then in the native and effective state. Solid forms of anti-EGFR antibodies according to the invention are thus also suitable for the preparation of delayed-release formulations, which are advantageous for the patient since administration is only necessary at relatively large time intervals. Pharmaceutical preparations according to the invention can also be injected directly into the tumour and thus develop their action directly at the site of action as intended.

The medicaments adapted to parenteral administration include aqueous and non-aqueous sterile injection solutions comprising antioxidants, buffers, bacteriostatics and solutes, by means of which the formulation is rendered isotonic with the blood of the recipient to be treated; as well as aqueous and non-aqueous sterile suspensions, which can comprise suspension media and thickeners. The formulations can be delivered in single-dose or multi-dose containers, for example sealed ampoules and vials, and stored in the freeze-dried (lyophilised) state, so that only the addition of sterile carrier liquid, for example water for injection purposes, immediately before use is necessary. Injection solutions and suspensions prepared in accordance with the formulation can be prepared from sterile powders, granules and tablets.

The solid forms of anti-EGFR antibodies according to the invention, optionally in redissolved form, can also be administered in the form of liposome supply systems, such as, for example, small unilamellar vesicles, large unilamellar vesicles and multilamellar vesicles. Liposomes can be formed from various phospholipids, such as, for example, cholesterol, stearylamine or phosphatidylcholines.

The solid forms of anti-EGFR antibodies according to the invention and variants thereof in precipitated, redissolved or suspended form can also be coupled with soluble polymers as targeted medicament excipients. Such polymers can encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The solid forms of anti-EGFR antibodies may furthermore be coupled to a class of biodegradable polymers which are suitable for achieving slow release of a medicament, for example polylactic acid, poly-epsilon-caprolactone, polyhydroxybutyric acid, polyorthoesters, polyacetals, polydihydroxypyrans, polycyanoacrylates, polylactic-co-glycolic acid, polymers, such as conjugates between dextran and methacrylates, polyphosphoesters, various polysaccharides and polyamines and poly-ε-caprolactone, albumin, chitosan, collagen or modified gelatine and crosslinked or amphipathic block copolymers of hydrogels.

Medicaments adapted to transdermal administration can be delivered as independent plasters for extended, close contact with the epidermis of the recipient. Thus, for example, the active ingredient can be supplied from the plaster by means of iontophoresis, as described in general terms in Pharmaceutical Research, 3(6), 318 (1986).

Medicaments adapted to topical administration can be formulated as ointments, creams, suspensions, lotions, powders, solutions, pastes, gels, sprays, aerosols or oils.

For treatment of the eye or other external tissue, for example mouth and skin, the formulations are preferably administered as a topical ointment or cream. In the case of formulation as an ointment, the active ingredient can be employed either with a paraffinic or a water-miscible cream base. Alternatively, the active ingredient can be formulated to give a cream with an oil-in-water cream base or a water-in-oil base.

Medicaments adapted to topical administration to the eye include eye drops, where the active ingredient is dissolved or suspended in a suitable excipient, in particular an aqueous solvent.

Medicaments adapted to rectal administration can be delivered in the form of suppositories or enemas.

Medicaments adapted to administration by inhalation encompass finely particulate dusts or mists which can be produced by means of various types of pressurised dispensers with aerosols, atomisers or insufflators. For the purposes of the present invention, particular preference is given to powders of solid forms of anti-EGFR antibodies according to the invention for administration as inhalant.

Medicaments adapted to vaginal administration can be delivered as pessaries, tampons, creams, gels, pastes, foams or spray formulations.

It goes without saying that, besides the constituents particularly mentioned above, the medicaments according to the invention may also comprise other agents usual in the sector with relation to the particular type of pharmaceutical formulation.

The invention furthermore relates to sets (kits) consisting of separate packs of
a) an effective amount of a precipitate and/or crystal of an anti-EGFR antibody, preferably of a monoclonal anti-EGFR antibody, particularly preferably of Mab C225 (cetuximab) or Mab h425 (EMD 72000) and/or variants or fragments thereof in precipitated, redissolved or suspended form, and
b) an effective amount of a further medicament active ingredient.

The set contains suitable containers, such as boxes or cartons, individual bottles, bags or ampoules. The set may, for example, contain separate ampoules each containing an effective amount of a solid form according to the invention, optionally in redissolved form, and an effective amount of a further medicament active ingredient in dissolved or lyophilised form.

A therapeutically effective amount of a solid form of an anti-EGFR antibody according to the invention depends on a number of factors, including, for example, the age and weight, the precise disease state requiring treatment, and its severity, the nature of the formulation and the method of administration, and is ultimately determined by the treating doctor or veterinarian. However, an effective amount of an anti-EGFR antibody according to the invention for the treatment of neoplastic growth, for example intestinal or breast cancer, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg would usually be between 70 and 700 mg, where this amount can be given as a single dose per day or usually in a series of sub-doses (such as, for example, two, three, four, five or six) per day, so that the total daily dose is the same. The suitable antibody titre is determined by methods known to the person skilled in the art. The dose proposed for administration is generally sufficient to achieve the desired tumour-inhibiting action. However, the dose should also be chosen to be as low as possible so that no side effects, such as undesired cross reactions, anaphylactic reactions or the like, occur.

The invention furthermore relates to the use of solid forms according to the invention for the preparation of a medicine which comprises the biologically active antibody and/or one of its variants and/or fragments in precipitated non-crystalline, precipitated crystalline or in dissolved or suspended form.

Medicines according to the invention can be used, in particular, for the prophylaxis and/or treatment of diseases and disease states. The invention therefore relates to the use of solid forms of anti-EGFR antibodies according to the invention, preferably of monoclonal anti-EGFR antibodies, particularly preferably of Mab C225 (cetuximab) or Mab h425 (EMD 72000) and/or variants or fragments thereof in precipitated, redissolved or suspended form for the preparation of a medicine for the treatment and/or prophylaxis of diseases.

It has been shown in various in-vitro and in-vivo studies that blockage of the EGFR by antibodies against tumours at various levels, for example by inhibiting the proliferation of cancer cells, reducing tumour-mediated angiogenesis, induction of cancer cell apoptosis and increasing the toxic effects of radiation therapy and conventional chemotherapy.

Medicaments comprising solid forms of the antibodies according to the invention in redissolved or suspended form are able effectively to regulate, modulate or inhibit EGFR and can therefore be employed for the prevention and/or treatment of diseases in connection with unregulated or disturbed EGFR activity. In particular, the solid forms of anti-EGFR antibodies according to the invention can therefore be employed in the treatment of certain forms of cancer and in illnesses caused by pathological angiogenesis, such as diabetic retinopathy or inflammation.

The invention therefore furthermore relates to the use of solid forms according to the invention in precipitated, redissolved or resuspended form for the preparation of a medicine for the treatment and/or prophylaxis of diseases caused, mediated and/or propagated by EGFR and/or by EGFR-mediated signal transduction.

Medicaments according to the invention are particularly suitable for the treatment and/or prophylaxis of cancer, including solid carcinomas, such as, for example, carcinomas (for example of the lungs, pancreas, thyroid, bladder or colon), myeloid illnesses (for example myeloid leukaemia) or adenomas (for example villous colonic adenoma), pathological angiogenesis and metastatic cell migration. The medicaments are furthermore useful in the treatment of complement activation-dependent chronic inflammation (Niculescu et al. (2002) Immunol. Res., 24:191-199) and immunodeficiency induced by HIV-1 (human immunodeficiency virus type 1) (Popik et al. (1998) J Virol, 72: 6406-6413).

In addition, the present medicaments are suitable as pharmaceutical active ingredients for mammals, in particular for humans, in the treatment of EGFR-induced diseases. The term "EGFR-induced diseases" relates to pathological states which are dependent on EGFR activity. EGFR is involved directly or indirectly in signal transduction pathways of various cell activities, including proliferation, adhesion and migration, as well as differentiation. The diseases associated with EGFR activity include the proliferation of tumour cells, pathological neovascularisation, which promotes the growth of solid tumours, neovascularisation in the eye (diabetic retinopathy, age-induced macular degeneration and the like) and inflammation (psoriasis, rheumatoid arthritis and the like).

The illnesses discussed here are usually divided into two groups, hyperproliferative and non-hyperproliferative illnesses. In this connection, psoriasis, arthritis, inflammation, endometriosis, scarring, benign prostate hyperplasia, immunological diseases, autoimmune diseases and immunodeficiency diseases are regarded as non-cancerous diseases, of which arthritis, inflammation, immunological diseases, autoimmune diseases and immunodeficiency diseases are usually regarded as non-hyperproliferative illnesses.

In this connection, brain cancer, lung cancer, squamous cell carcinoma, bladder cancer, stomach cancer, pancreatic cancer, liver cancer, kidney cancer, colorectal cancer, breast cancer, head cancer, neck cancer, oesophageal cancer, gynaecological cancer, thyroid cancer, lymphoma, chronic leukaemia and acute leukaemia are to be regarded as cancerous illnesses, all of which are usually counted amongst the group of hyperproliferative illnesses. In particular, cancerous cell growth and in particular cancerous cell growth mediated directly or indirectly by EGFR is an illness which represents a target of the present invention.

It can be shown that the medicaments according to the invention have an in-vivo antiproliferative action in a xenotransplant tumour model. The medicaments according to the invention are administered to a patient with a hyperproliferative illness, for example for inhibiting tumour growth, for reducing the inflammation associated with a lymphoproliferative illness, for inhibiting transplant rejection or neurological damage owing to tissue repair, etc. The present medicaments are useful for prophylactic or therapeutic purposes. As used herein, the term "treat" is used as reference both to the prevention of diseases and to the treatment of existing complaints. The prevention of proliferation is achieved by administration of the medicaments according to the invention before development of the evident disease, for example for preventing tumour growth, preventing metastatic growth, reducing restenosis associated with cardiovascular surgery, etc. Alternatively, the medicaments are used for the treatment of continuing diseases by stabilising or improving the clinical symptoms of the patient. The host or patient can belong to any mammalian species, for example a primate species, particularly humans; rodents, including mice, rats and hamsters; rabbits, horses, cows, dogs, cats, etc. Animal models are of interest for the experimental studies, providing a model for the treatment of human disease.

The receptivity of a certain cell to treatment with the medicaments according to the invention can be determined by in-vitro tests. Typically, a culture of the cell is incubated with a medicament according to the invention at different concentrations for a period which is sufficient to enable the active ingredients to induce cell death or inhibit migration, usually between about one hour and one week. In-vitro tests can be carried out using cultivated cells from a biopsy sample. The vital cells remaining after the treatment are then counted.

The dose varies depending on the specific medicaments used, the specific illness, the patient status, etc. Typically, a therapeutic dose is sufficient in order considerably to reduce the undesired cell population in the target tissue, while the vitality of the patient is maintained. The treatment is generally continued until a considerable reduction has occurred, for example a reduction of at least about 50% of the specific cell count, and can be continued until essentially no undesired cells are detected in the body.

Various assay systems are available for identification of EGFR inhibitors. In the scintillation proximity assay (Sorg et al., J. of. Biomolecular Screening, 2002, 7, 11-19) and the flashplate assay, the radioactive phosphorylation of a protein or peptide as substrate is measured using γATP. In the presence of an inhibitory compound, a reduced radioactive signal or none at all can be detected. Furthermore, homogeneous time-resolved fluorescence resonance energy transfer (HTR-FRET) and fluorescence polarisation (FP) technologies are useful as assay methods (Sills et al., J. of Biomolecular Screening, 2002, 191-214).

Other non-radioactive ELISA assay methods use specific phospho-antibodies (phospho-ABs). The phospho-AB only binds the phosphorylated substrate. This binding can be detected using a second peroxidase-conjugated anti-sheep antibody by chemiluminescence (Ross et al., 2002, Biochem. J., just about to be published, manuscript BJ20020786).

There are many illnesses and disease states associated with deregulation of cell proliferation and of cell death (apoptosis). The illnesses and disease states which can be treated, prevented or ameliorated by medicaments according to the invention include the illnesses and disease states listed below, but are not restricted thereto. The medicaments according to the invention are useful in the treatment and/or prophylaxis of a number of different illnesses and disease states which involve proliferation and/or migration of smooth muscle cells and/or inflammation cells in the intimal layer of a vessel, resulting in restricted blood flow through this vessel, for example in neointimal occlusive lesions. Occlusive transplant vessel illnesses of interest include atherosclerosis, coronary vascular disease after transplantation, vein transplant stenosis, peri-anastomotic prosthesis restenosis, restenosis after angioplasty or stent placement and the like.

The present invention relates to the use of the medicaments according to the invention for the treatment or prevention of cancer. The invention therefore particularly preferably relates to the use of solid forms of anti-EGFR antibodies according to the invention for the preparation of a medicine for the treatment and/or prophylaxis of tumours and/or tumour metastases, where the tumour is particularly preferably selected from the group consisting of brain tumour, tumour of the urogenital tract, tumour of the lymphatic system, stomach tumour, laryngeal tumour, monocytic leukaemia, lung adenocarcinoma, small-cell lung carcinoma, pancreatic cancer, glioblastoma and breast carcinoma, without being restricted thereto.

The invention furthermore relates to the use of medicaments according to the invention for the preparation of a medicine for the treatment of diseases selected from the group consisting of cancerous illnesses consisting of squamous cell carcinoma, bladder cancer, stomach cancer, liver cancer, kidney cancer, colorectal cancer, breast cancer, head cancer, neck cancer, oesophageal cancer, gynaecological cancer, pancreatic cancer, lymphoma, chronic leukaemia and acute leukaemia.

The medicaments according to the invention can be administered to patients for the treatment of cancer. The present medicaments inhibit tumour angiogenesis and thus influence the growth of tumours (J. Rak et al. Cancer Research, 55:4575-4580, 1995). The angiogenesis-inhibiting properties of the medicaments according to the invention are also suitable for the treatment of certain forms of blindness associated with retinal neovascularisation.

The invention therefore also relates to the use of solid forms of anti-EGFR antibodies according to the invention in precipitated, redissolved or suspended form for the preparation of a medicine for the treatment and/or prophylaxis of diseases caused, mediated and/or propagated by angiogenesis.

A disease of this type involving angiogenesis is an eye disease, such as retinal vascularisation, diabetic retinopathy, age-induced macular degeneration and the like.

The invention therefore also relates to the use of solid forms of anti-EGFR antibodies according to the invention in precipitated, redissolved or suspended form for the preparation of a medicine for the treatment and/or prophylaxis of diseases selected from the group consisting of retinal vascularisation, diabetic retinopathy, age-induced macular degeneration and/or inflammation diseases.

The invention furthermore relates to the use of medicaments according to the invention for the treatment and/or prophylaxis of diseases selected from the group consisting of psoriasis, rheumatoid arthritis, contact dermatitis, late-type oversensitivity reaction, inflammation, endometriosis, scarring, benign prostate hyperplasia, immunological diseases, autoimmune diseases and immunodeficiency diseases.

The invention also relates to the use of medicaments according to the invention for the treatment and/or prophylaxis of bone pathologies selected from the group consisting of osteosarcoma, osteoarthritis and rachitis.

The medicaments according to the invention can furthermore be used to provide additive or synergistic effects in certain existing cancer chemotherapies and irradiations, and/or can be used to restore the efficacy of certain existing cancer chemotherapies and irradiations.

The invention therefore also relates to the use of solid forms of anti-EGFR antibodies according to the invention in precipitated, redissolved or suspended form for the preparation of a medicament for the treatment and/or prophylaxis of diseases in which a therapeutically effective amount of a solid form according to the invention in precipitated, redissolved or suspended form is administered in combination with a compound from the group consisting of 1) oestrogen receptor modulator, 2) androgen receptor modulator, 3) retinoid receptor modulator, 4) cytotoxic agent, 5) antiproliferative agent, 6) prenyl protein transferase inhibitors, 7) HMG-COA reductase inhibitors, 8) HIV protease inhibitors, 9) reverse transcriptase inhibitors, 10) growth factor receptor inhibitors and 11) angiogenesis inhibitors.

The invention therefore also relates to the use of solid forms of anti-EGFR antibodies according to the invention in precipitated, redissolved or suspended form for the preparation of a medicament for the treatment and/or prophylaxis of diseases in which a therapeutically effective amount of a solid form according to the invention in precipitated, redissolved or suspended form is administered in combination with radiotherapy and a compound from the group consisting of 1) oestrogen receptor modulator, 2) androgen receptor modulator, 3) retinoid receptor modulator, 4) cytotoxic agent, 5) antiproliferative agent, 6) prenyl protein transferase inhibitors, 7) HMG-COA reductase inhibitors, 8) HIV protease inhibitors, 9) reverse transcriptase inhibitors, 10) growth factor receptor inhibitors and 11) angiogenesis inhibitors.

The medicaments according to the invention can thus also be administered together with other well-known therapeutic agents that are selected for their particular usefulness against the condition that is being treated. For example, in the case of bone conditions, combinations that would be favourable include those with antiresorptive bisphosphonates, such as alendronate and risedronate; integrin blockers (as defined further below), such as $\alpha v \beta 3$ antagonists; conjugated oestrogens used in hormone replacement therapy, such as Prempro®, Premarin® and Endometrion®; selective oestrogen receptor modulators (SERMs), such as raloxifene, droloxifene, CP-336.156 (Pfizer) and lasofoxifene; cathepsin K inhibitors; and ATP proton pump inhibitors.

The present medicaments are also suitable for combination with known anti-cancer agents. These known anti-cancer agents include the following: oestrogen receptor modulators, androgen receptor modulators, retinoid receptor modulators, cytotoxic agents, antiproliferative agents, prenyl protein transferase inhibitors, HMG-COA reductase inhibitors, HIV protease inhibitors, reverse transcriptase inhibitors, growth factor inhibitors and angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethyl-propanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other $5\alpha$-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, $\alpha$-difluoromethylornithine, ILX23-7553, trans-N-(4'-hydroxyphenyl)retinamide and N-4-carboxyphenyl retinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans)-bis-mu-(hexane-1,6-diamine)-mu-[diamine-platinum(II)]bis[diamine(chloro)platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)-propanamine, 1-amino-9-ethyl-5-fluoro-2,3-dihydro-9-hydroxy-4-methyl-1H, 12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido [4,3-b]carbazole-1-carboxamide, asulacrine, (5a,5aB,8aa, 9b)-9-[2-[N-[2-(dimethyl-amino)ethyl]-N-methylamino] ethyl]-5-[4-hydroxy-3,5-dimethoxyphenyl]-5,5a,6,8,8a,9-hexohydrofuro(3',4':6,7)naphto(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2-(diethylamino) ethylamino]-7-methoxy-9-oxo-9H-thioxanthen-4-ylmethyl] formamide, N-(2-(dimethyl-amino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides, such as G3139, ODN698, RVASK-RAS, GEM231 and INX3001, and antimetabolites, such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-di-hydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies against growth factors other than those listed above under "angiogenesis inhibitors", such as trastuzumab, and tumour suppressor genes, such as p53, which can be delivered via recombinant virus-mediated gene transfer (see U.S. Pat. No. 6,069,134, for example). Medicaments according to the invention can also be administered in combination with all other therapeutic antibodies known to the person skilled in the art or pharmaceutical active ingredients which are suitable in connection with the above-mentioned diseases.

Furthermore, solid forms according to the invention of antibodies according to the invention in precipitated, redissolved or suspended form can be used for the isolation and investigation of the activity or expression of EGFR. In addition, they are particularly suitable for use in diagnostic methods for illnesses in connection with unregulated or disturbed EGFR activity. The invention therefore furthermore relates to the use of solid forms of anti-EGFR antibodies according to the invention in precipitated, redissolved or suspended form as activators or inhibitors of EGFR, particularly preferably as inhibitors of EGFR.

For diagnostic purposes, antibodies according to the invention can, for example, be radioactively labelled. A preferred labelling method is the iodogen method (Fraker et al., 1978). For diagnostic purposes, the antibody is particularly preferably used as the F(ab')2 fragment. Excellent results are achieved thereby, meaning that background subtraction is unnecessary. Fragments of this type can be prepared by known methods (e.g. Herlyn et al., 1983). In general, pepsin digestion is carried out at an acidic pH, and the fragments are separated from undigested IgG and fragments of heavy chains by protein A Sepharose™ chromatography.

The precipitates and/or crystals according to the invention preferably exhibit an advantageous biological activity which can easily be detected in enzyme assays, as described in the examples. In enzyme-based assays of this type, the antibodies according to the invention preferably exhibit and cause an inhibiting effect, which is usually documented by $IC_{50}$ values in a suitable range, preferably in the micromolar range and more preferably in the nanomolar range.

Determination Methods:

Regarding determination methods, the present invention encompasses all determination methods known to the person skilled in the art or from the literature.

Crystalline structures can be determined, for example, with reference to diffraction spectra in the X-ray diffraction measurement. In particular, crystalline structures of antibodies according to the invention can be determined by microscopic studies using polarising filters. Further determination methods, without being restricted thereto, encompass electron photomicrographs.

The determination of protein size, structural integrity, purity or glycosylation pattern of the solid forms according to the invention in precipitated, redissolved or resuspended form encompasses, without being restricted thereto, SE-HPLC, peptide mapping (digestion), N-terminal sequencing, SDS page, TRIS/glycine gradient gel (non-reducing), the FTIR (Fourier transform infrared spectra) method, CD (circular dichroism), RAMAN spectroscopy, carbohydrate staining (PAS method), oligosaccharide profiling, determination of the monosaccharide composition and isoelectric focusing.

The stability of solid forms or formulations according to the invention can, for example, be determined, without being restricted thereto, with the aid of stability programmes, for example storage at 25° C. and 60% relative atmospheric humidity and at 40° C. and 70% relative atmospheric humidity over an extended period and determination of the stability or structural integrity of the protein at regular intervals, for example by the above-mentioned determination methods (SE-HPLC, FT-IR, SDS-PAGE (reducing or non-reducing)).

Methods for the determination of the biological activity or efficacy of solid forms according to the invention in precipitated crystalline, precipitated non-crystalline, dissolved or suspended form encompass, for example, without being restricted thereto, ELISA, biological cell assays, FTIR or CD.

Methods for the determination of reduced aggregation tendency of solid forms forms according to the invention in precipitated crystalline, precipitated non-crystalline, dissolved or suspended form and thus the possibility of preparing highly concentrated formulations, the crystal size or precipitate size encompass, for example, without being restricted thereto, visual inspection, sub-visible particles analysis, nephelometry or turbidimetry or dynamic light scattering characterisation.

Above and below, all temperatures are indicated in ° C. In the following examples, "conventional work-up" means that water is added if necessary, and, if necessary, the pH is adjusted to between 2 and 10, depending on the constitution of the end product.

EXAMPLE 1

Agents and Precipitation and/or Crystallisation Conditions Which Can Be Used in Accordance with the Invention The following list includes in each case all feasible hydrates, related salts and derivatives of the said compounds which are known to the person skilled in the art.
1. Precipitation Reagents:
    1.1 Salts:
    for example sodium acetate trihydrate, potassium chloride, sodium chloride, trisodium citrate dihydrate, dipotassium hydrogenphosphate, disodium hydrogenphosphate dihydrate, ammonium sulfate, ammonium acetate, ammonium bromide, ammonium chloride, triammonium citrate, diammonium hydrogencitrate, ammonium dihydrogenphosphate, diammonium hydrogenphosphate, diammonium tartrate, citric acid monohydrate, imidazole, potassium acetate, potassium bromide, tripotassium citrate monohydrate, potassium dihydrogenphosphate, potassium sulfate, magnesium acetate tetrahydrate, magnesium bromide hexahydrate, magnesium chloride hexahydrate, magnesium sulfate heptahydrate, sodium dihydrogenphosphate monohydrate, sodium sulfate decahydrate, proline, succinic acid, zinc acetate dihydrate, zinc sulfate heptahydrate
    1.2 Polymers:
    for example polyethylene glycol (PEG):
    cyclodextrins, dextran, sodium carboxymethylcellulose (Na-CMC), poloxamer, polyacrylic acid, polyethylene glycol monomethyl ether (mPEG), polypropylene glycol (PPG), polyvinyl alcohol (PVA), polyvinylpyrrolidone (PVP)
    1.3 Organic Solvents:
    for example ethanol, glycerol
2. Adjuvants:
    for example viscosity-modifying substances, detergents (for example Tween®, Solutol® HS 15, Pluronic®), Cremophor® EL, Avacel® 20, polyoxyethylene sorbitan monooleate), reducing agents (glutathione, 2-mercaptoethanol, dithiothreitol), complexing agents (EDTA, EGTA)
3. Buffers:
    for example phosphate buffer: Na (or K) phosphate; also with addition of isotonicity agents (for example NaCl (or KCl)), possible pH about 6.0-8.2 citrate buffer: Na citrate or citric acid, possible pH about 2.2-6.5; also with addition of isotonicity agents (for example NaCl); other salts are also conceivable for the isotonisation.
    succinate buffer: pH about 4.8-6.3
    acetate buffer: sodium acetate, pH about 2.5-6
    histidine buffer: pH about 6.0-7.8
    glutamic acid: pH 8.0 to 10.2
    glycine (N,N-bis(2-hydroxyethyl)glycine): pH about 8.6 to 10.6
    glycinate buffer: pH about 6.5-7.5
    imidazole: pH 6.2 to 7.8
    potassium chloride: pH about 1.0 to 2.2
    lactate buffer: pH about 3.0-6.0
    maleate buffer: pH about 2.5-5.0
    tartrate buffer: pH about 3.0-5.0
    TRIS: pH about 6.8-7.7
    phosphate/citrate buffer
4. pH Range:
    The theoretically conceivable pH is pH 4-10, preferably pH 5-9
5. Temperature Range:
    The theoretically conceivable temperature range is the temperature from −10° C. to 40° C.; preferably 0-25° C., particularly preferably from 4° C. to 20° C.
6. Stabilisers:
    6.1 Amino Acids:
    for example arginine, ornithine, lysine, histidine, glutamic acid, aspartic acid, isoleucine, leucine, alanine, phenylalanine, tyrosine, tryptophan, methionine, serine, proline
    6.2 Sugars and Sugar Alcohols:
    for example sucrose, lactose, glucose, mannose, maltose, galactose, fructose, sorbose, raffinose, trehalose, glucosamine, N-methylglucosamine, galactosamine, neuramic acid
    6.3 Antioxidants:
    for example acetone sodium bisulfite, ascorbic acid, ascorbic acid esters, butylhydroxyanisole (BHA), butylhydroxytoluene (BHT), cysteine, nordihydroguaiaretic acid (NDGA), monothioglycerol, sodium bisulfite, sodium metabisulfite, tocopherols, glutathione
    6.4 Preservatives:
    for example m-cresol, chlorocresol, phenol, benzyl alcohol, methylparaben, propylparaben, butylparaben, chlorobutanol, phenyl mercury nitrate, phenyl mercury acetate, thimersal, benzalkonium chloride, benzethonium chloride
    6.5 Cyclodextrins:
    for example hydroxypropyl-β-cyclodextrin, sulfobutylethyl-β-cyclodextrin, γ-cyclodextrin, α-cyclodextrin
    6.6 Albumins:
    for example human serum albumin (HSA), bovine serum albumin (BSA)
    6.7 Polyhydric Alcohols:
    for example glycerol, ethanol, mannitol
    6.8 Salts:
    for example acetate salts (for example sodium acetate), magnesium chloride, calcium chloride, tromethamine, EDTA (for example Na-EDTA)
7. Isotonicity Agents:
    for example sodium chloride, potassium chloride, glucose, glycerol, dextrose, sodium chloride, sodium sulfate

EXAMPLE 2

Crystallisation of Erbitux™ with Ammonium Sulfate

500 µl of protein (20 mg/ml in 10 mM phosphate, pH 8.0)
400 µl of buffer (10 mM phosphate, pH 8.0)
100 µl of precipitant (saturated ammonium sulfate solution in 10 mM phosphate, pH 8.0)

The addition of the precipitation reagents to the protein solution is carried out in solution (batch process). After the pipetting, the sample should be mixed by "hand shaking". The process can be carried out at room temperature or 4° C.

EXAMPLE 3

Crystallisation of Erbitux™ with Ethanol

500 µl of protein (20 mg/ml in 10 mM citrate, pH 5.5)
400 µl of buffer (10 mM citrate, pH 5.5)
100 µl of precipitant (50% (v/v) of ethanol in 10 mM citrate, pH 5.5)
or
500 µl of protein (20 mg/ml in 10 mM citrate, pH 5.5)
500 µl of precipitant (50% (v/v) of ethanol in 10 mM citrate, pH 5.5)

The addition of the precipitation reagents to the protein solution is carried out in solution (batch process). After the pipetting, the sample should be mixed by "hand shaking". The process can be carried out at room temperature or 4° C.

EXAMPLE 4

Precipitation of Erbitux™ With Ammonium Sulfate

500 µl of protein (20 mg/ml in 10 mM phosphate, pH 8.0)
500 µl of precipitant (saturated ammonium sulfate solution in 10 mM phosphate, pH 8.0)
or
200 µl of protein (20 mg/ml in 10 mM phosphate, pH 8.0)
800 µl of precipitant (saturated ammonium sulfate solution in 10 mM phosphate, pH 8.0)
or
500 µl of protein (20 mg/ml in 10 mM citrate, pH 5.5)
500 µl of precipitant (saturated ammonium sulfate solution in 10 mM citrate, pH 5.5)
or
200 µl of protein (20 mg/ml in 10 mM citrate, pH 5.5)
800 µl of precipitant (saturated ammonium sulfate solution in 10 mM citrate, pH 5.5)

The addition of the precipitation reagents to the protein solution is carried out in solution (batch process). After the pipetting, the sample should be mixed by "hand shaking". The process can be carried out at room temperature or 4° C.

EXAMPLE 5

Precipitation of Erbitux™ With PEG

500 µl of protein (20 mg/ml in 10 mM phosphate, pH 8.0)
500 µl of precipitant (50% (w/v) of PEG 4000 in 10 mM phosphate, pH 8.0)
or
500 µl of protein (20 mg/ml in 10 mM citrate, pH 5.5)
500 µl of precipitant (50% (w/v) of PEG 4000 in 10 mM citrate, pH 5.5)
or
500 µl of protein (20 mg/ml in 10 mM phosphate, pH 8.0)
500 µl of precipitant (50% (w/v) of PEG 8000 in 10 mM phosphate, pH 8.0)
or
500 µl of protein (20 mg/ml in 10 mM citrate, pH 5.5)
500 µl of precipitant (50% (w/v) of PEG 8000 in 10 mM citrate, pH 5.5)

The addition of the precipitation reagents to the protein solution is carried out in solution (batch process). After the pipetting, the sample should be mixed by "hand shaking". The process can be carried out at room temperature or 4° C.

EXAMPLE 6

Microscopic Investigation of the Crystal Form

The crystals obtained in Examples 1 and 2 were investigated by microscopy. Both the birefringent properties which are typical of crystals and the stainability with Coomassie Brilliant Blue which is typical of proteins were detected.

Crystals having a size of about 50-200 µm were found.

EXAMPLE 7

Investigation of the Precipitates for Nativity

The precipitates obtained in Examples 4 and 5 were redispersed and investigated by FT-IR spectrometry. The amide I-2. derivation spectra of the starting material before precipitation and of the redispersed precipitate were congruent.

EXAMPLE 8

Performance of the Crystallisation Method Described in WO02072636

In order to check the results from Patent Application WO02072636, it was first attempted, in a control experiment as described in WO02072636, to obtain crystals which can subsequently be used as seed crystal by means of the Wizard I screen. Although needle-shaped crystals were obtained under the precipitation conditions using calcium chloride or calcium acetate, they were, however, likewise formed in citrate buffer solution without protein. Thus, the needle-shaped crystals described are obtained both from the protein solution and the negative control (without protein) using the process described in WO02072636. It is clear from this that these are presumably at best protein inclusions in crystals of the precipitation reagent.

We claim:

1. A crystal of chimeric monoclonal antibody c225 (cetuximab) which remains a biologically active antibody protein when dissolved or suspended in an aqueous medium, said crystal being obtained by a process comprising incubating an aqueous solution or suspension of said c225 antibody with a precipitation reagent comprising ammonium sulfate, sodium acetate, sodium citrate, potassium phosphate, PEG and/or ethanol, for a time sufficient to allow formation of said crystal.

2. A process for the preparation of a crystal of chimeric monoclonal antibody c225 (cetuximab) which remains a biologically active antibody protein when dissolved or suspended in an aqueous medium, said process comprising incubating an aqueous solution or suspension of said c225 antibody with a precipitation reagent comprising ammonium sulfate, sodium acetate, sodium citrate, potassium phosphate, PEG and/or ethanol, for a time sufficient to allow formation of said crystal, and separating and isolating the crystal thereof.

3. A process according to claim 2, which is carried out in batch format.

4. A storage-stable medicament which comprises a crystal of claim 1 together with a stabilizing agent.

5. A pharmaceutical preparation which comprises a pharmaceutically acceptable carrier and the crystal according to claim 1, wherein said c225 antibody concentration is 50-150 mg/ml.

6. The crystal according to claim 1, which has a size of 50-200 μm.

7. The crystal according to claim 1, wherein the precipitation reagent comprises saturated ammonium sulfate solution in 10 mM phosphate, pH 8.0.

8. The crystal according to claim 1, wherein the precipitation reagent comprises 50% (v/v) of ethanol in 10 mM citrate, pH 8.0.

* * * * *